United States Patent [19]

Yoshida et al.

[11] Patent Number: 5,087,742
[45] Date of Patent: Feb. 11, 1992

[54] PROCESS FOR PREPARING AROMATIC POLYCARBOXYLIC ACIDS

[75] Inventors: Kazuo Yoshida, Iwaki; Nobuyuki Okubo, Tokyo; Toshiharu Matsuda, Iwaki; Yutaka Konai, Machida, all of Japan

[73] Assignee: Kureha Kagaku Kogyo K.K., Japan

[21] Appl. No.: 538,057

[22] Filed: Jun. 14, 1990

[30] Foreign Application Priority Data

Jul. 20, 1989 [JP] Japan .................... 1-186062

[51] Int. Cl.$^5$ .................... C07C 51/245; C07C 49/213
[52] U.S. Cl. .................... 562/421; 562/480; 568/331
[58] Field of Search .................... 562/421; 568/331

[56] References Cited

U.S. PATENT DOCUMENTS

| | | | |
|---|---|---|---|
| 4,317,919 | 3/1982 | Jones et al. | 562/414 |
| 4,665,215 | 5/1987 | Davenport | 560/130 |
| 4,670,581 | 6/1987 | Tanigaki | 560/108 |
| 4,709,088 | 11/1987 | Hirose et al. | 562/414 |

OTHER PUBLICATIONS

Chemical Abstracts, vol. 46, 9544, Corresponding to J. Org. Chem. 16, pp. 1785-7 (1951).
Keizo Kinoshita, Bull. Chem. Soc. Japan, 34 pp. 783-787 (1959).
David D. Neiswender Jr. et al., J. Am. Chem. Soc., 82, pp. 2876-8 (1960).
Kazuhiro Maruyama, Bull. Chem. Soc. Japan, 34, pp. 103-104 (1961).
J. Org. Chem. 41, pp. 1077-1078 (1976).
Kenneth N. Carter et al., J. Org. Chem. 47, pp. 2208-2210 (1982).
Stephen O. Nwaukwa et al., Tetrahedron Letters, vol. 23, No. 31, pp. 3135-8 (1982).
L. M. Sayre et al., J. Org. Chem., vol. 49, pp. 3498-3503 (1984).
J. William Suggs et al., Tetrahedron Letters, vol. 27, No. 4, pp. 437-440 (1986).

*Primary Examiner*—José G. Dees
*Assistant Examiner*—Vera C. Clarke
*Attorney, Agent, or Firm*—Lowe, Price, LeBlanc & Becker

[57] ABSTRACT

A process for preparing aromatic polycarboxylic acids is disclosed, wherein a benzil derivative is oxidized with molecular oxygen in the presence of an oxidation catalyst consisting substantially of at least one heavy metal catalyst selected from cobalt and manganese and a bromine catalyst in a solvent containing at least 50 wt.% of an aliphatic monocarboxylic acid having at most three carbon atoms.

According to this invention, there are provided 4,4'-bis(4-alkylphenyl)benzils (wherein alkyl is methyl, ethyl or isopropyl), which are novel benzil derivative.

9 Claims, 6 Drawing Sheets

PROCESS FOR PREPARING AROMATIC POLYCARBOXYLIC ACIDS

FIELD OF THE INVENTION

This invention relates to a process for the preparation of aromatic polycarboxylic acids and more specifically, to a process for the preparation of aromatic dicarboxylic acids or aromatic tricarboxylic acids, wherein a benzil derivative having lower alkyl groups as side chains on the aromatic rings is oxidized.

The present invention is also concerned with 4,4'-bis(4-alkylphenyl)benzils which are novel benzil derivatives useful as raw materials of aromatic polycarboxylic acids, particularly, 4,4'-biphenyldicarboxylic acid.

BACKGROUND OF THE INVENTION

With respect to aromatic polycarboxylic acids, for example, 4,4'-biphenyldicarboxylic acid is useful as a raw material for high-performance polyesters, aramide resins, etc., and trimellitic acid is useful as a plasticizer for polyvinyl chloride and a raw material for polyamide-imide resins.

If such aromatic polycarboxylic acids can be obtained efficiently by one-stage oxidative reaction making use of, as a raw material, a benzil derivative having lower alkyl groups as side chains on the aromatic rings, this has a great significance in industrial technique.

By the way, in order to prepare an aromatic polycarboxylic acid by one-stage oxidative reaction from such a benzil derivative, it is necessary to oxidatively cleave an 1,2-diketone linkage (—COCO—) bonding two aromatic rings so as to convert two carbonyl groups thereof into carboxyl groups and at the same time, to oxidize the alkyl groups of the side chains into carboxyl groups.

The following various processes have been known heretofore as processes for oxidatively cleaving the 1,2-diketone linkage of benzil (namely, dibenzoyl):

(1) A process wherein benzil is reacted with 95% aqueous hydrogen peroxide into benzoic acid in the presence of 70% perchloric acid in acetic acid [J. Org. Chem., 16, 1785–7 (1951)].

(2) A process wherein benzil is reacted into benzoic acid in the presence of a complex of cuprous chloride and pyridine as a catalyst in methanol while introducing air [Bull. Chem. Soc. Jpn 32, 783–87 (1959)].

(3) A process wherein benzil is oxidized with sodium hypochlorite into benzoic acid under strong alkali (4) A process wherein benzil is reacted with tert-butyl peroxide into benzoic acid in the presence of potassium hydroxide in chlorobenzene [Bull. Chem. Soc. Jpn 34, 102–4 (1961)].

(5) A process wherein benzil is reacted with potassium superoxide into benzoic acid in the presence of 18-crown-6-ether in benzene [J. Org. Chem., 41, 1077–8 (1976)].

(6) A process wherein benzil is reacted with hydroxylamine sulfonic acid in formic acid to concurrently conduct oximization and Beckmann rearrangement into benzoic acid [J. Org. Chem., 47, 2208–10 (1982)].

(7) A process wherein benzil is reacted with calcium hypochlorite into benzoic acid in a mixed solvent of acetonitrile and acetic acid [Tetrahedron Lett., 23, 3135–8 (1982)].

(8) A process wherein benzil is reacted with a cupric nitrate-pyridine-triethylamine complex into benzoic acid in methanol [J. Org. Chem., 49, 3498–3503 (1984)].

(9) A process wherein benzil is oxidized with dioxobis(trifluoroacetato)chromium into benzoic acid [Tetrahedron Lett., 27, 437–40 (1986)].

However, none of the above processes are suitable for a process wherein alkyl groups and an 1,2-diketone linkage (two carbonyl groups) of the benzil derivative having the alkyl groups as the side chains on the aromatic rings are concurrently oxidized into carboxyl groups to prepare an aromatic polycarboxylic acid by one-stage oxidative reaction.

Namely, by the processes (1) and (4), it is possible to oxidatively cleave said two carbonyl groups, but it is difficult to oxidize the alkyl groups bonded to the aromatic rings as side chains into carboxyl groups. With respect to the processes (2) and (8), the active species of the catalysts are Cu ions. These species have the ability to cleave said two carbonyl groups. However, it is also impossible to oxidize the alkyl groups bonded to the aromatic rings. By the process (3), an activated methyl or methylene group is oxidized into a carboxyl group. A side-chain alkyl group in toluic acid (namely, methylbenzoic acid) or the like is hard to be oxidized. Therefore, it is difficult to oxidize the side-chain alkyl groups at the same time that the 1,2-diketone linkage is oxidatively cleaved. The process (5) is difficult to practice industrially because it is not economical due to the use of an expensive crown ether. In the process (6), compounds formed by the cleavage of said two carbonyl groups are aromatic monocarboxylic acids or amides thereof. Another step is hence required to oxidize their side-chain alkyl groups. Also, by the process (7), only the oxidative cleavage of the 1,2-diketone linkage can be achieved, but the side-chain alkyl groups must be oxidized by another step. The process (9) involves a defect that the yield of the oxidative cleavage reaction itself to the 1,2-diketone linkage is low.

As described above, it is possible to oxidatively cleave the 1,2-diketone linkage of benzil or a benzil derivative into carboxylic groups by using any one of the above-described processes. However, it is difficult or substantially impossible to prepare an aromatic polycarboxylic acid by one-stage oxidative reaction from a benzil derivative having alkyl groups as side chains on the aromatic rings. These processes are hence accompanied by a defect that the process for preparing the aromatic polycarboxylic acid becomes at least two stages because at least one different step is required to oxidize each of the alkyl groups as the side chains.

OBJECTS AND SUMMARY OF THE INVENTION

It is an object of the present invention to provide a process for the preparation of an aromatic polycarboxylic acid by one-stage oxidative reaction from a benzil derivative having alkyl groups as side chains on the aromatic rings.

Another object of this invention is to provide novel benzil derivatives useful as raw materials for aromatic polycarboxylic acids, particularly, 4,4'-biphenyldicarboxylic acid.

The present inventors have carried out an extensive investigation with a view toward solving the above-mentioned defects of the prior art. As a result, it has been found that when a specific benzil derivative having alkyl groups as side chains on the aromatic rings is oxidized with molecular oxygen in the presence of an oxidation catalyst consisting substantially of at least one heavy metal catalyst selected from cobalt and manganese and a bromine catalyst in a solvent containing at least 50 wt. % of an aliphatic monocarboxylic acid having at most three carbon atoms, an aromatic polycarboxylic acid can be efficiently obtained by one-stage oxidative reaction.

In addition, the present inventors have synthesized 4,4'-bis(4-alkylphenyl)benzils which are novel benzil derivatives. It has also be found that these benzil derivatives are useful as raw materials for 4,4'-biphenyldicarboxylic acid which is an aromatic polycarboxylic acid.

The present invention has been led to completion on the basis of these findings.

According to the present invention, there is thus the process for the preparation of an aromatic polycarboxylic acid, which comprises oxidizing a benzil derivative represented by the following formula I:

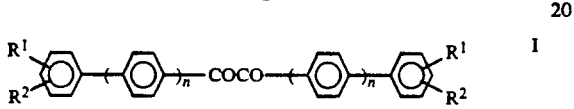

wherein $R^1$ means a hydrogen atom, or a methyl, ethyl or isopropyl group, $R^2$ denotes a methyl, ethyl or isopropyl group, and n stands for 0 or 1, with molecular oxygen under the following conditions:

(a) in a solvent containing at least 50 wt. % of an aliphatic monocarboxylic acid having at most three carbon atoms;

(b) in the presence of an oxidation catalyst consisting substantially of at least one heavy metal catalyst selected from the group consisting of cobalt and manganese in an amount of 0.0003-0.17 gram atom in terms of elemental metal per 100 g of the solvent;

(c) in the presence of a bromine catalyst in an amount of 0.0001-0.05 gram atom in terms of element bromine per 100 g of the solvent;

(d) at a reaction temperature in the range of from 80° to 220° C.;

(e) at an oxygen partial pressure in the range of from 0.1 to 8 kg/cm in terms of absolute pressure.

According to this invention, there are also provided 4,4'-bis(4-alkylphenyl)benzils represented by the following general formula 5 [II]:

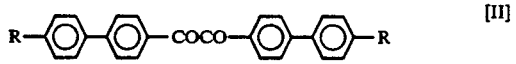

wherein R means a methyl, ethyl or isopropyl group. Namely, there are provided 4,4'-bis(4-methylphenyl)benzil represented by the formula [III]:

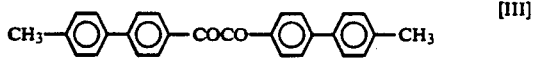

4,4'-bis(4-ethylphenyl)benzil represented by the formula [IV]:

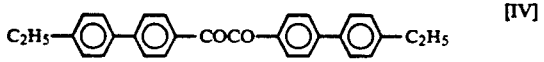

and 4,4'-bis(4-isopropylphenyl)benzil represented by the formula [V]:

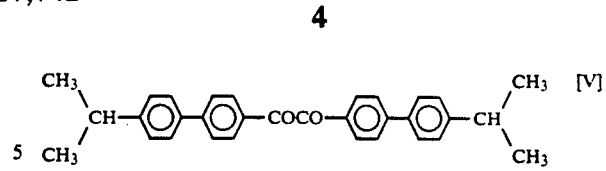

BRIEF DESCRIPTION OF THE DRAWINGS

FIGS. 1 and 4, FIGS. 2 and 5, and FIGS. 3 and 6 indicate the cases where the alkyl groups of 4,4'-bis(4-alkylphenyl)benzils are methyl, ethyl and isopropyl groups respectively.

DETAILED DESCRIPTION OF THE INVENTION

Figure 1:
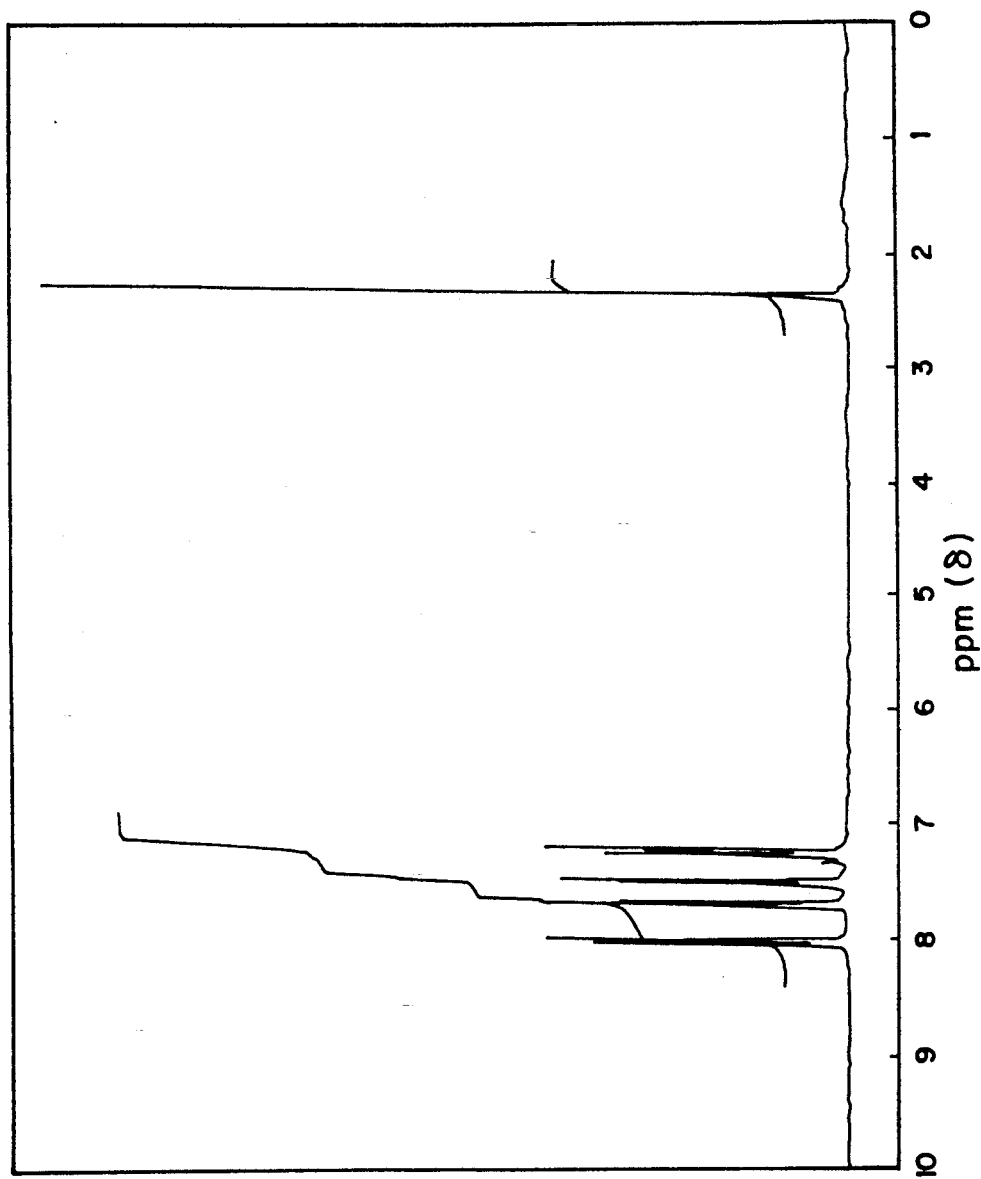
FIGS. 1 through 3 illustrate nuclear magnetic resonance ($^1$H-NMR) spectra of 4,4'-bis(4-alkylphenyl)benzils according to this invention

Features of the present invention will hereinafter be described in detail.

Benzil derivative

As exemplary benzil derivatives used in the present invention and represented by the above formula [I], may be mentioned 4,4'-dimethylbenzil, 4,4'-diethylbenzil, 4,4'-diisopropylbenzil, 3,3',4,4'-tetramethylbenzil, 2,2',4,4'-tetramethylbenzil, 2,2',5,5'-tetramethylbenzil, 4,4'-bis(4-methylphenyl)benzil, 4,4'-bis(4-ethylphenyl)benzil, 4,4'-bis(4-isopropylphenyl)benzil.

Of these, 4,4'-bis(4-alkylphenyl)benzils (wherein the alkyl group is a methyl, ethyl or isopropyl group) are novel compounds and can be synthesized with ease by the Friedel-Crafts reaction of oxalyl dihalide and 4-alkylbiphenyl in the presence of a Lewis acid catalyst.

The above benzil derivatives other than the 4,4'-bis(4-alkylphenyl)benzils can also be obtained by the Friedel-Crafts reaction of a substituted aromatic compound such as toluene, ethylbenzene, cumene or xylene and oxalyl dihalide in the presence of a Lewis acid catalyst. For example, when toluene is used as the substituted aromatic compound, 4,4'-dimethylbenzil is formed. Beside, the use of ethylbenzene, cumene, o-xylene, m-xylene and p-xylene result in the formation of 4,4'-diethylbenzil, 4,4'-diisopropylbenzil, 3,3',4,4'-tetramethylbenzil, 2,2',4,4'-tetramethylbenzil and 2,2',5,5'-tetramethylbenzil respectively.

Oxidation catalyst

As oxidation catalysts useful in the practice of this invention, are used oxidation catalysts consisting substantially of:

(1) at least one heavy metal catalyst selected from cobalt and manganese; and (2) a bromine catalyst.

The cobalt catalyst and manganese catalyst used in this invention may be either a simple substance or a compound so long as they are in a form soluble in the oxidative reaction system.

As specific examples of such compounds, may be mentioned inorganic compounds such as oxides, hydroxides, carbonates, basic carbonates and halides of cobalt and manganese; and their salts with organic acids, for example, fatty acids such as formic acid, acetic acid and propionic acid, naphthenic acid and aromatic carboxylic acids. Of these, the bromides and fatty acid salts are preferred with the acetic acid salts being particularly preferred.

The cobalt and manganese catalysts may be used either singly or in combination with each other in an optional proportion. It is however preferable to use a mixed catalyst containing Co and Mn in a proportion of 1:99 to 95:5 in terms of an atomic ratio.

The amount of the cobalt catalyst and/or manganese catalyst to be used is a total of at least 0.0003 gram atom, preferably 0.003–0.17 gram atom in terms of element metal based on 100 g of a solvent. The selectivity of the aromatic polycarboxylic acid is more improved as the total amount of these heavy catalysts to be used is increased. The upper limit of the total amount of the heavy metal catalysts to be used depends upon their solubility in a solvent. However, if they are used in a total amount exceeding 0.17 gram atom in terms of element metal based on 100 g of the solvent, no sharp improvement in selectivity is recognized. It is hence inadvisable from the economical point of view to use the heavy catalysts in such an amount.

On the other hand, as exemplary bromine catalysts, may be mentioned molecular bromine; hydrogen bromide; inorganic bromides such as salts of hydrobromic acid; alkyl bromides such as methyl bromide and ethyl bromide; and brominated fatty acids such as bromoacetic acid. No particular limitation is imposed on the bromine catalyst so long as it is dissolved in a solvent to generate bromine ions. In particular, ammonium bromide, hydrogen bromide and potassium bromide are preferred from the viewpoint of selectivity, easiness in handling, etc.

The bromine catalyst generates bromine ions in the reaction system and can permit to form an aromatic polycarboxylic acid with high selectivity by using it in combination with at least one heavy metal catalyst described above.

The amount of the bromine catalyst to be used is at least 0.0001 gram atom, preferably 0.001–0.05 gram atom based on 100 g of a solvent. If the amount of the bromine catalyst to be used should be too little, the rate of formation of the polycarboxylic acid will become slow. On the other hand, if the amount should be too great, there will be a potential problem that bromine bonds to the aromatic rings to increase the proportion of by-products formed. It is hence not preferable to use the bromine catalyst in any amounts outside the above range.

The bromine catalyst may be added to the reaction system from the beginning, but it may be added at once or gradually after the formation of an oxidative intermediate
in the reaction system.

Solvent

With respect to the solvents useful in the practice of this invention, it is only necessary to contain an aliphatic monocarboxylic acid having at most three carbon atoms in an amount of at least 50 wt. % of the solvent.

As exemplary aliphatic monocarboxylic acid having at most three carbon atoms, may be mentioned formic acid, acetic acid and propionic acid. Among others, acetic acid is preferred.

To these aliphatic monocarboxylic acids, may be added at least one of other solvents, for example, water, aldehydes such as paraformaldehyde and ketones such as methyl ethyl ketone, if necessary.

Among the other solvents, water is particularly preferred because when it is caused to contain in an amount of 0.1 wt. % or more, the yield of the aromatic polycarboxylic acid can be enhanced even if the amounts of the oxidation catalyst to be used are equal to each other.

With respect to the amount of the solvent to be used, it is only necessary to be an amount capable of dissolving at least part of the benzil derivative as a raw material and the oxidation catalyst therein. No particular limitation is imposed on such an amount. However, it is generally used at a weight ratio of 2–100 times the raw material. If the amount of the solvent to be used should be unduly little, the flowability of the reaction system will be lowered, whereby a smooth reaction is prevented. On the contrary, if the solvent is used in an unduly large amount, the reaction itself is not accelerated correspondingly. It is hence inadvisable to use the solvent in such an unduly large amount.

Reaction conditions

Besides pure oxygen, mixed gases composed of pure oxygen diluted with other inert gases, and air may be used as the molecular oxygen.

A reaction temperature is generally 80°–220° C., preferably 120°–200° C. If the temperature of the reaction system should be too low, the rate of reaction will become slow. On the contrary, if the temperature should be too high, oxidative decomposition of the solvent will tend to occur. Such an unduly low or high temperature is hence not preferred.

The oxidative reaction according to this invention may occur under atmospheric pressure, but proceeds faster under pressure. The pressure of the oxidative reaction system may be any pressure not lower than a pressure necessary for keeping the solvent to a liquid phase. In addition, it is better for the partial pressure of oxygen to be high. In general, the partial pressure of oxygen is preferably 0.1–8 kg/cm$^2$ (absolute pressure). In the case of air or molecular oxygen diluted with an inert gas such as nitrogen, a range of 0–30 kg/cm$^2$ in terms of gauge pressure is satisfactory to its total pressure.

The oxidative reaction may be either a batch reaction or a successive reaction.

ADVANTAGES OF THE INVENTION

According to the preparation process of this invention, it is possible to concurrently effect the oxidative cleavage of the 1,2-diketone linkage in a benzil derivative and the oxidation of side-chain alkyl group on the aromatic rings into carboxyl groups by one-stage reaction. In addition, it is possible to provide aromatic polycarboxylic acids of the intended compounds in a high yield. The process is hence of great value in industry.

Furthermore, according to this invention, there can be provided 4,4'-bis(alkylphenyl)benzils which are novel benzil derivatives useful as raw materials for 4,4'-biphenyldicarboxylic acid.

EMBODIMENTS OF THE INVENTION

The present invention will hereinafter be described more specifically by the following examples. It should however be borne in mind that this invention is not limited to the following examples only.

EXAMPLES 1–3

A 200-cc titanium-made autoclave equipped with a stirrer, reflux condenser and air inlet tube was charged with 2.00 g of 2,2',4,4'-tetramethylbenzil (TMBZ), 100 g of acetic acid (AcOH) and their corresponding oxidation catalyst and water shown in Table 1. After the autoclave was pressurized with nitrogen to 10 kg/cm² (gauge pressure), the resultant mixture was heated.

When the temperature of the reaction system reached 80° C., air was introduced at a rate of 24 l/hr under stirring while maintaining the pressure of the autoclave to 10 kg/cm² (gauge pressure) to conduct an oxidative reaction for 6 hours. After the reaction, the resulting trimellitic acid (TMA) was analyzed by gas chromatography. It was found that yields shown in Table 1 were attained.

The gas-chromatographic analysis was conducted by using a 2-m glass column charged with "Chromosorb WAW DMCS" (80-100 mesh) on which 5% of "DEXSIL 300GC" had been supported (product of Gasukuro Kogyo Inc.) and measuring under heating each sample to 100°-270° C. at a rate of 10° C./min. A detector used was an FID. Incidentally, each of the samples used was prepared by trimethylsilylating with bis(trimethylsilyl)-trifluoroacetamide after removing the heavy metals of the catalysts in advance. In the following examples, the gas-chromatographic analysis followed the method in Example 1.

TABLE 1

| | Formation of trimellitic acid by oxidizing 2,2',4'4'-tetramethylbenzil | | |
|---|---|---|---|
| Example | 1 | 2 | 3 |
| TMBZ (g) | 2.00 | 2.00 | 2.00 |
| AcOH (g) | 100 | 100 | 100 |
| Co*¹ (g) | 0.50 | 6.40 | 0.50 |
| Co (gram atom) | 0.002 | 0.026 | 0.002 |
| Mn*² (g) | 1.00 | 18.90 | 1.00 |
| Mn (gram atom) | 0.004 | 0.077 | 0.004 |
| NH₄Br (g) | 1.00 | 1.00 | 1.00 |
| Br (gram atom) | 0.010 | 0.010 | 0.010 |
| H₂O (g) | 0 | 0 | 7.12 |
| Yield of TMA (%) | 29.1 | 80.8 | 77.2 |

*¹Co: Cobalt acetate tetrahydrate.
*²Mn: Manganese acetate tetrahydrate.

EXAMPLE 4

An oxidative reaction was conducted by the same apparatus and under the same conditions as in Example 2 except that 4,4'-bis(4-methylphenyl)benzil (synthesized in accordance with the procedure of Example 8) was used instead of 2,2',4,4'-tetramethylbenzil.

After the reaction, the resulting product was similarly analyzed by the gas chromatography. The yield of 4,4'-biphenyldicarboxylic acid was found to be 82.4%.

EXAMPLE 5

Using the same apparatus as that in Example 1, the apparatus was charged with 2.00 g of 4,4'-bis(4-methylphenyl)benzil, 100 g of acetic acid, 0.50 g of cobalt acetate tetrahydrate (Co: 0.002 gram atom) and 1.00 g of manganese acetate tetrahydrate (Mn: 0.004 gram atom). After the apparatus was pressurized with nitrogen to 5 kg/cm² (gauge pressure), air was introduced at a rate of 24 l/hr under stirring while maintaining the same pressure to conduct an oxidative reaction for 6 hours.

The resulting product was similarly analyzed by the gas chromatography. The yields of 4,4'-biphenyldicarboxylic acid and 4-methyl-4'-biphenylcarboxylic acid were found to be 10.5% and 80.0% respectively.

Successively, 1.00 g of ammonium bromide was added to the reaction system, and the apparatus was pressurized again to 5 kg/cm² (gauge pressure) to conduct an oxidative reaction at 150° C. for 4 hours. As a result, the yield of 4,4'-biphenyldicarboxylic acid was increased to 91.2%.

EXAMPLE 6

Using the same apparatus as that in Example 1, the apparatus was charged with 2.00 g of 4,4'-bis(4-ethylphenyl)benzil (synthesized in accordance with the procedure of Example 9), 100 g of acetic acid, 0.50 g of cobalt acetate tetrahydrate (Co: 0.002 gram atom), 1.00 g of manganese acetate tetrahydrate (Mn: 0.004 gram atom), 1.00 g of ammonium bromide (Br: 0.010 gram atom) and 9.50 g of water. After the apparatus was pressurized with nitrogen to 10 kg/cm² (gauge pressure), the resulting mixture was heated up to 180° C. while maintaining the same pressure and air was then introduced at a rate of 24 l/hr under stirring to conduct an oxidative reaction for 6 hours.

The resulting product was similarly analyzed by the gas chromatography. It was found that 4,4'-biphenyldicarboxylic acid was obtained in a yield of 81.5%.

EXAMPLE 7

Using the same apparatus as that in Example 1, the apparatus was charged with 2.00 g of 4,4'-bis(4-isopropylphenyl)benzil (synthesized in accordance with the procedure of Example 10), 100 g of acetic acid, 6.40 g of cobalt acetate tetrahydrate (Co: 0.026 gram atom), 18.90 g of manganese acetate tetrahydrate (Mn: 0.077 gram atom) and 1.00 g of ammonium bromide (Br: 0.010 gram atom). After the apparatus was pressurized with nitrogen to 15 kg/cm² (gauge pressure), the resulting mixture was heated up to 180° C. while maintaining the same pressure and air was then introduced at a rate of 24 l/hr under stirring to conduct an oxidative reaction for 6 hours.

The resulting product was similarly analyzed by the gas chromatography. It was found that 4,4'-biphenyldicarboxylic acid was obtained in a yield of 85.1%.

Synthesis examples of novel 4,4'-bis(4-alkylphenyl)-benzils according to this invention are given in the following Examples 8–10.

EXAMPLE 8

A 50-ml three-necked flask equipped with a condenser and dropping funnel was charged with 3.36 g (20.0 mmoles) of 4-methylbiphenyl, 2.66 g (19.9 mmoles) of ground aluminum chloride and 10 ml of dichloromethane, and the resulting mixture was maintained to 0° C. A solution of 0.86 ml (10.1 mmoles) of oxalyl chloride in 5 ml of dichloromethane was added dropwise into the mixture through the dropping funnel over 50 minutes. 4-Methylbiphenyl vanished in 2.5 hours after completion of the dropping.

After completion of the reaction, water was added while maintaining the temperature of the reaction mixture to 0.C to separate the catalyst and resulting product. A water phase was extracted with chloroform and the extract was combined with an organic phase separated previously. The combined organic phase was washed with water and then with a saturated saline solution, and further dewatered on anhydrous sodium sulfate. The extract was dried and solidified, thereby obtaining 3.78 g of solid component.

This solid component was analyzed by gas chromatography (column: "SE-30", 1 m) in accordance with the internal standard method. As a result, it was found that 4,4'-bis(4-methylphenyl)benzil was obtained in a yield of 4.4 mole % (based on oxalyl chloride). The thus-obtained crude crystals were recrystallized from toluene, thereby obtaining crystals having a DSC purity of 99.29%.

Incidentally, the DSC purity was determined by using a "DSC30" manufactured by Mettler Instrument AG. Upon the determination, the sample was heated from 160° C. to 225° C. at a heating rate of 2° C./min (this also applies to the subsequent examples).

EXAMPLE 9

The same apparatus as that in Example 8 was ged with 3.65 g (20.0 mmoles) of 4-ethylbiphenyl, 15 ml of dichloromethane and 0.86 ml (10.1 mmoles) of oxalyl chloride, and the resulting mixture was maintained to 0° C. Into the mixture, 2.66 g (19.9 mmoles) of finely-ground aluminum chloride was gradually added in three portions. 4-Ethylbiphenyl vanished in 3.5 hours after completion of the addition of aluminum chloride.

After completion of the reaction, 4.01 g of a solid component was obtained in accordance with the same procedure as in Example 8. This solid component was analyzed by the same method as in Example 8. As a result, it was found that 4,4'-bis(4-ethylphenyl)benzil was obtained in a yield of 0.5 mole % (based on oxalyl chloride).

The thus-obtained crude crystals were recrystallized from a mixed solvent of toluene and methanol in equivalent volumes, thereby obtaining crystals having a DSC purity of 9.74%.

EXAMPLE 10

The same apparatus as that in Example 8 was charged with 2.66 g (19.9 mmoles) of ground aluminum chloride and 10 ml of dichloromethane, and the resulting mixture was maintained to 0° C. Into the mixture, a mixed solution composed of 3.93 g (20.0 mmoles) of 4-isopropylbiphenyl, 0.86 ml (10.1 mmoles) of oxalyl chloride and 5 ml of dichloromethane was added dropwise through the dropping funnel over 90 minutes. 4-Isopropylbiphenyl vanished in 30 minutes after completion of the dropping.

After completion of the reaction, 4.14 g of a solid component was obtained in accordance with the same procedure as in Example 8. This solid component was analyzed by the same method as in Example 8. As a result, it was found that 4,4'-bis(4-isopropylphenyl)benzil was obtained in a yield of 61.7 mole %. After washing with heated hexane, the thus-obtained crude crystals were recrystallized from a mixed solvent of methanol and chloroform in equivalent volumes, thereby obtaining crystals having a DSC purity of 99.04%.

With the benzil derivatives obtained in Examples 8-10, $^1$H-NMR spectra and IR spectra are illustrated in FIGS. 1 through 3 and FIGS. 4 through 6 respectively.

In addition, the melting points and molecular weights (M+: measured by a gas chromatograph-mass spectrograph) of the benzil derivatives obtained in Examples 8-10 and their corresponding relations with the drawings are shown collectively in Table 2.

TABLE 2

Figure 2:
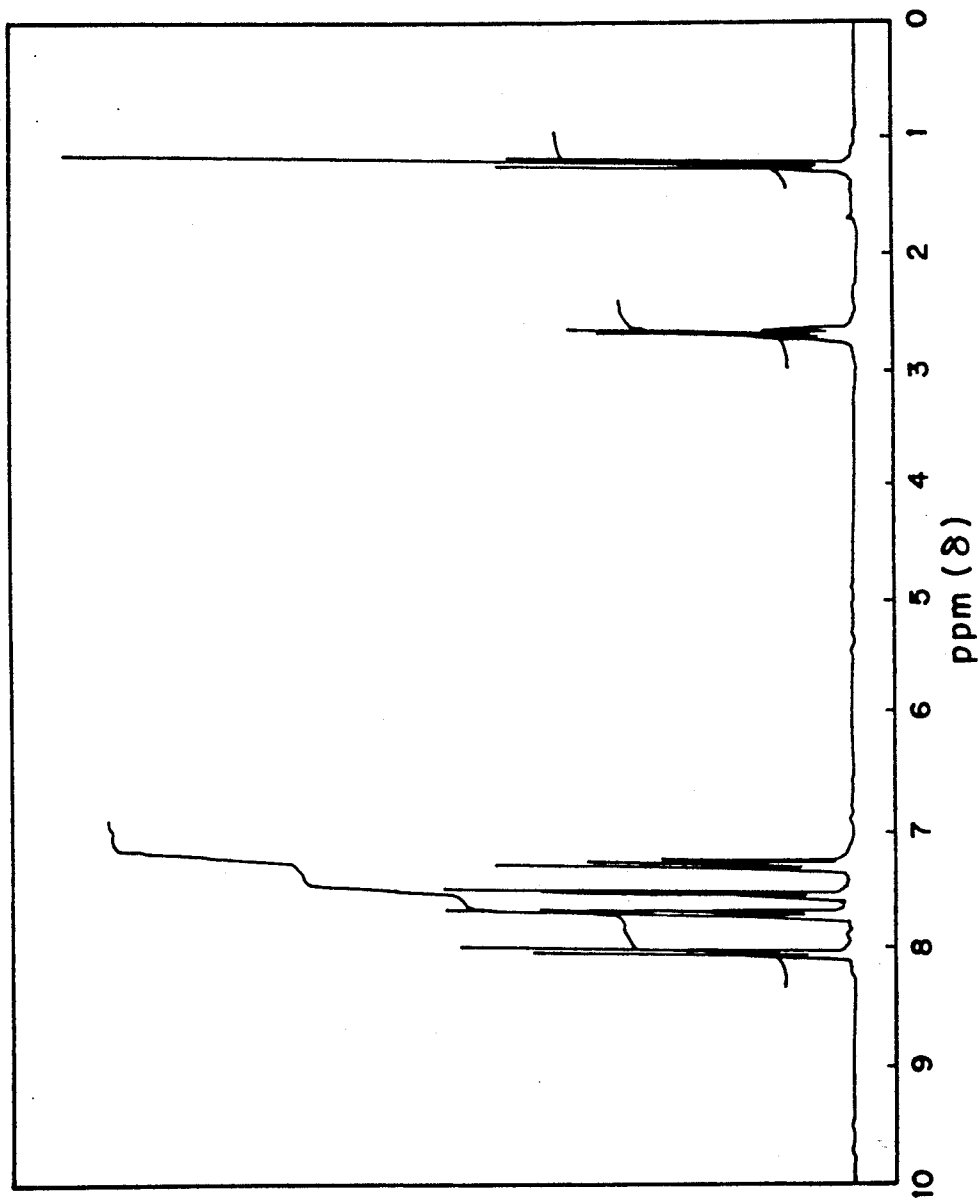
Figure 3:
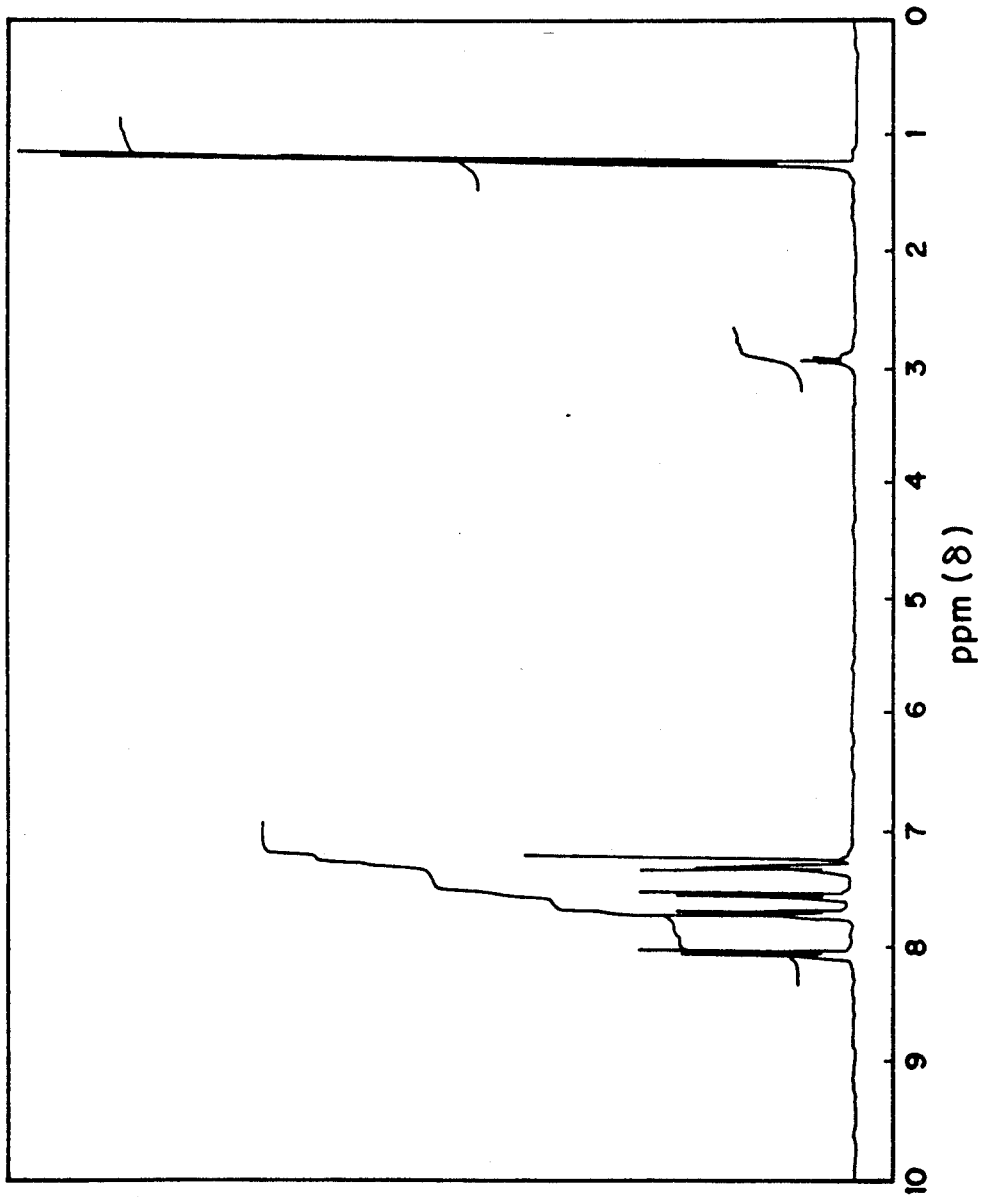

| Physical properties of 4,4'-bis(4-alkylphenyl)benzils | | | |
|---|---|---|---|
| Alkyl group | Methyl | Ethyl | Isopropyl |
| Melting point (°C.) | 220-221 | 196-197 | 171-172 |
| NMR | FIG. 1 | FIG. 2 | FIG. 3 |

TABLE 2-continued

Figure 4:
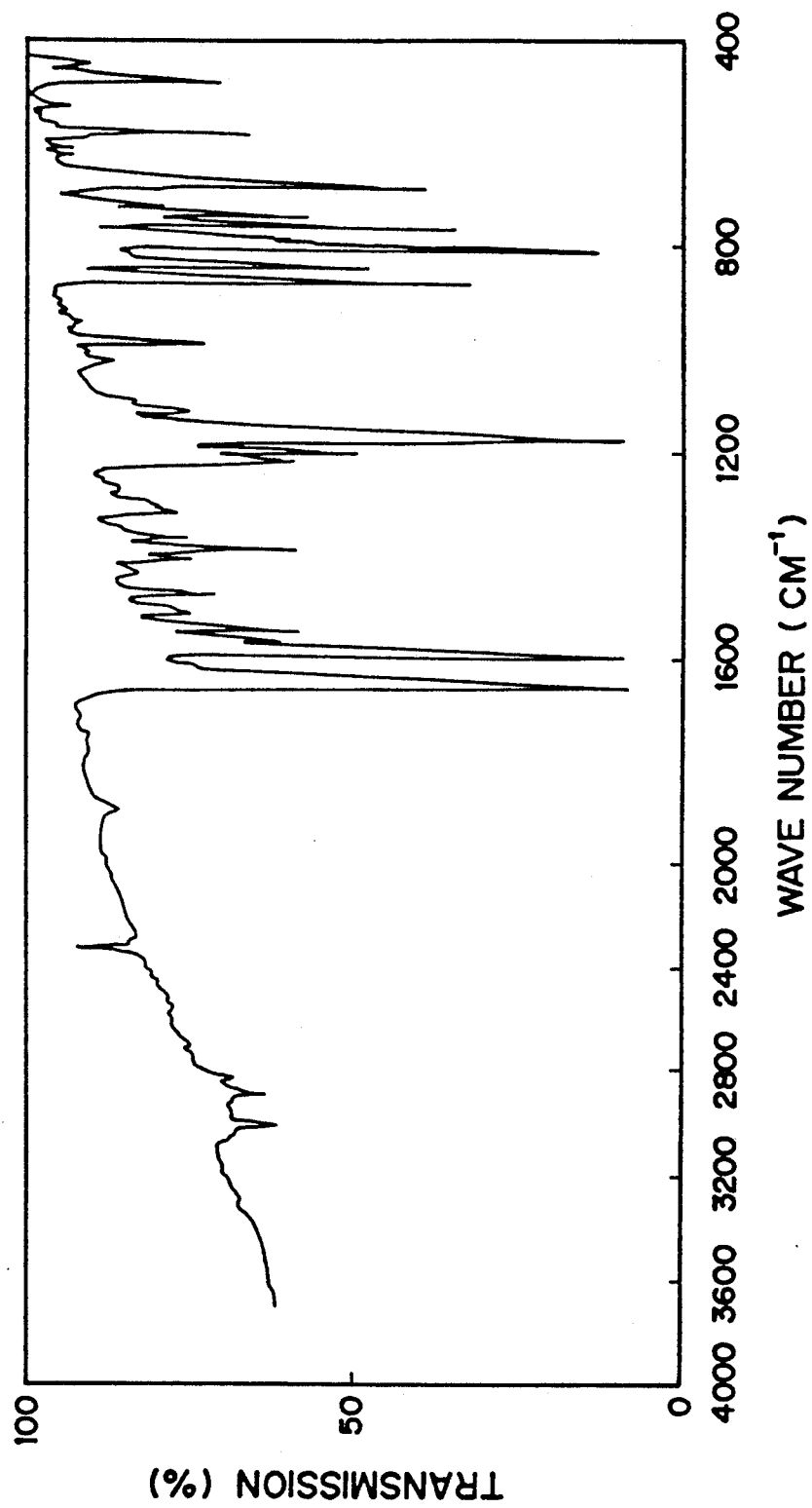
FIGS. 4 through 6 illustrate infrared absorption (IR) spectra of 4,4'-bis(4-alkylphenyl)benzils according to this invention.
Figure 5:
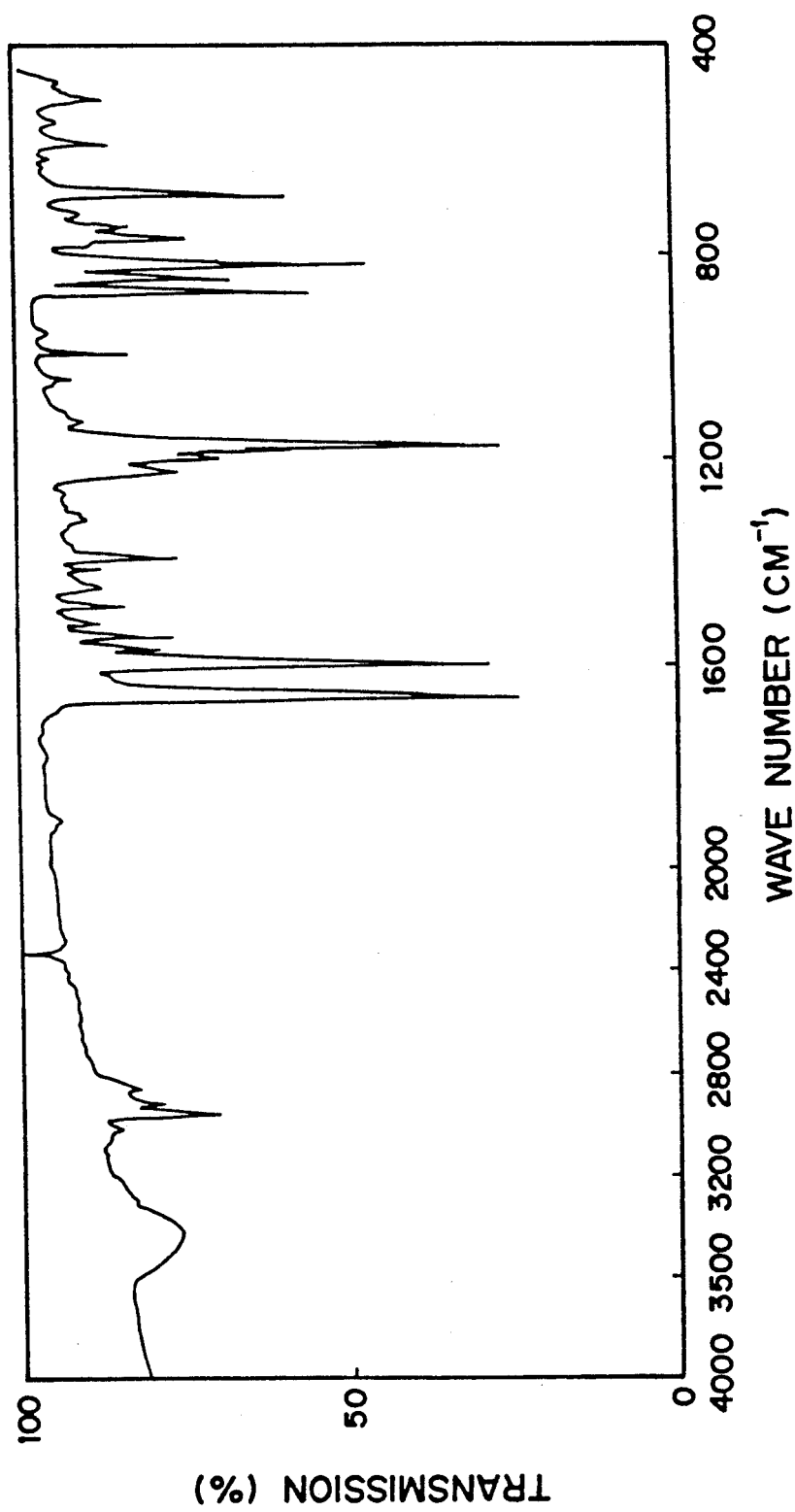
Figure 6:
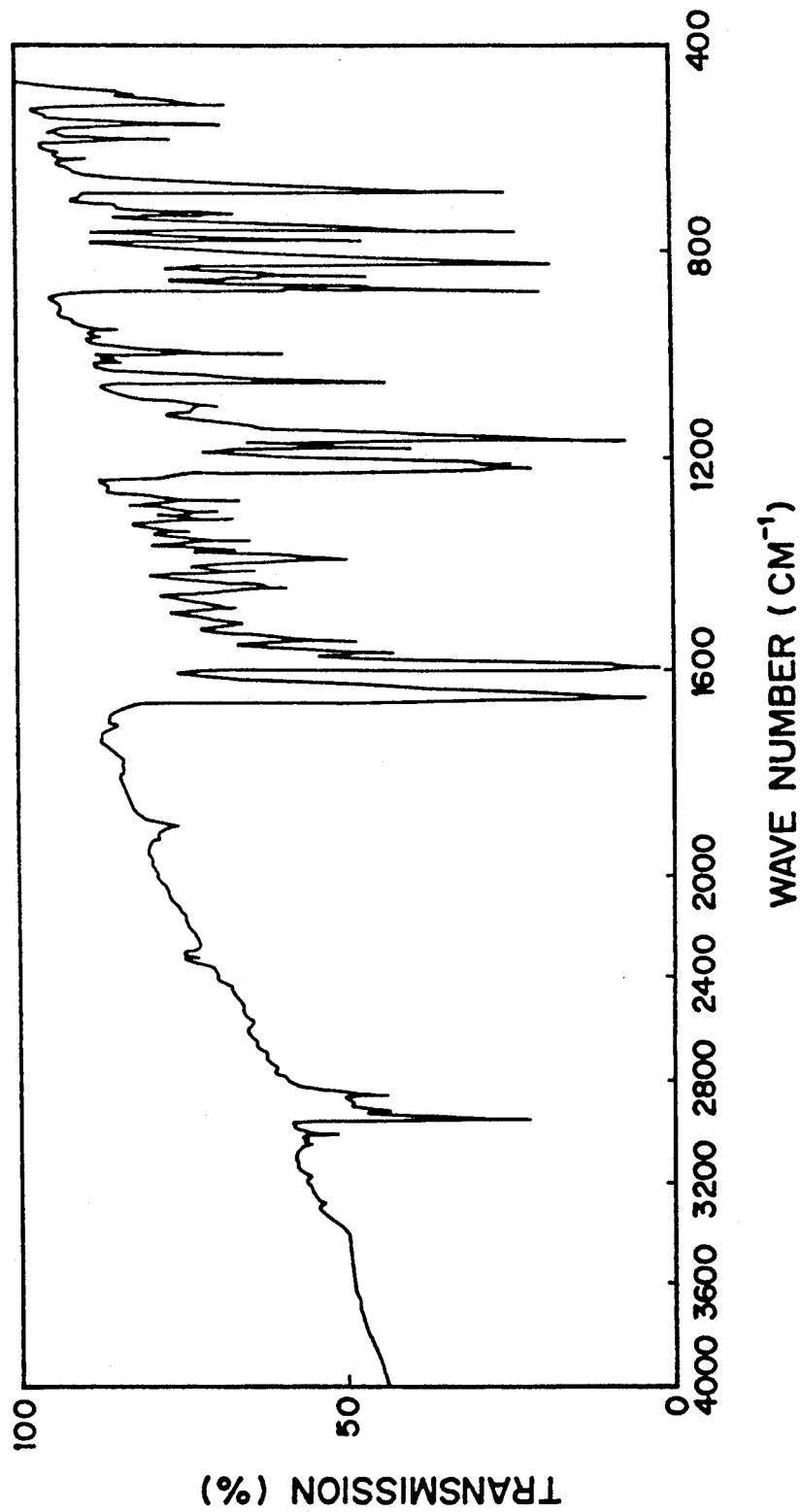

| Physical properties of 4,4'-bis(4-alkylphenyl)benzils | | | |
|---|---|---|---|
| Alkyl group | Methyl | Ethyl | Isopropyl |
| IR | FIG. 4 | FIG. 5 | FIG. 6 |
| M+ | 390 | 418 | 446 |

We claim:

1. A process for the preparation of an aromatic polycarboxylic acid, which comprises oxidizing a benzil derivative represented by the following formula I:

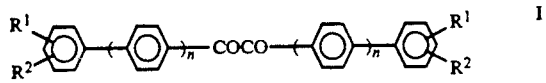

wherein $R^1$ means a hydrogen atom, or a methyl, ethyl or isopropyl group, $R^2$ denotes a methyl, ethyl or isopropyl group, and n stands for 0 or 1,
(a) in a solvent containing at least 50 wt. % of an aliphatic monocarboxylic acid having at most three carbon atoms;
(b) in the presence of an oxidation catalyst consisting susbtantially of at least one heavy metal catalyst selected from the group consisting of cobalt and manganese in an amount of 0.0003-0.17 gram atom in terms of elemental metal per 100 g of the solvent;
(c) in the presence of a bromine catalyst in an amount of 0.0001-0.05 gram atom in terms of element bromine per 100 g of the solvent;
(d) at a reaction temperature in the range of from 80° to 220° C.;
(e) at an oxygen partial pressure in the range of from 0.1 to 8 kg/cm² in terms of absolute pressure.

2. The process as claimed in claim 1, wherein the solvent is used at a weight ratio of 2-100 times the benzil derivative as a raw material.

3. The process as claimed in claim 1, wherein the solvent contains at least 0.1 wt. % of water.

4. The process as claimed in claim 1, wherein the aliphatic monocarboxylic acid is acetic acid.

5. The process as claimed in claim 1, wherein the benzil derivative is at least one compound selected from the group consisting of 4,4'-dimethylbenzil, 4,4'-diethylbenzil, 4,4'-diisopropylbenzil, 3,3',4,4'-tetramethylbenzil, 2,2',4,4'-tetramethylbenzil, 2,2',5,5'-tetramethylbenzil, 4,4'-bis(4-methylphenyl)benzil, 4,4'-bis(4-ethylphenyl)benzil, and 4,4'-bis(4-isopropylphenyl)benzil.

6. A 4,4'-bis(4-alkylphenyl)benzil represented by the following formula [II]:

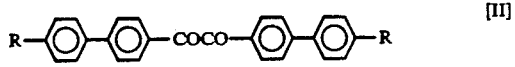

wherein R means a methyl, ethyl or isopropyl group.

7. The 4,4'-bis(4-alkylphenyl)benzil of claim 6, which is 4,4'-bis(4-methylphenyl)benzil represented by the formula [III]:

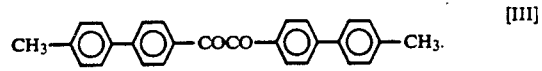

8. The 4,4'-bis(4-alkylphenyl)benzil of claim 6, which is 4,4'-bis(4-ethylphenyl)benzil represented by the formula [IV]:

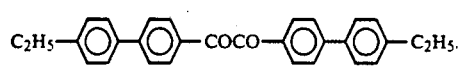  [IV]
9. The 4,4'-bis(4-alkylphenyl)benzil of claim 6, which is 4,4'-bis(4-isopropylphenyl)benzil represented by the formula [V]:
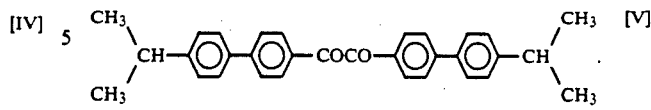  [V]
* * * * *